(12) United States Patent
Massoli et al.

(10) Patent No.: US 8,013,995 B2
(45) Date of Patent: Sep. 6, 2011

(54) METHOD AND APPARATUS FOR DETERMINING SIZE AND COMPOSITION OF A PARTICULATE MATTER IN A FUME FLOW

(75) Inventors: Patrizio Massoli, Capua (IT); Raffaela Calabria, Naples (IT); Roberto Morlacchi, Chiaravalle (IT); Rosario Quirino Iannone, Maddaloni (IT)

(73) Assignee: General Impianti S.r.l., Maiolati Spontini (IT)

( * ) Notice: Subject to any disclaimer, the term of this patent is extended or adjusted under 35 U.S.C. 154(b) by 0 days.

(21) Appl. No.: 12/847,224

(22) Filed: Jul. 30, 2010

(65) Prior Publication Data

US 2011/0026023 A1    Feb. 3, 2011

(30) Foreign Application Priority Data

Jul. 31, 2009    (IT) .............................. BO2009A0513

(51) Int. Cl.
*G01N 15/02*    (2006.01)
(52) U.S. Cl. .......................... 356/336; 356/337; 356/338
(58) Field of Classification Search .......... 356/335–343, 356/71–73; 250/574–575
See application file for complete search history.

(56) References Cited

U.S. PATENT DOCUMENTS

| | | | |
|---|---|---|---|
| 5,069,551 A * | 12/1991 | Brown | 356/432 |
| 5,104,221 A | 4/1992 | Bott et al. | |
| 5,155,047 A * | 10/1992 | Cioni et al. | 436/139 |
| 5,988,079 A * | 11/1999 | Carter | 110/185 |
| 6,067,157 A | 5/2000 | Altendorf | |
| 6,490,040 B1 * | 12/2002 | Berthold et al. | 356/438 |
| 6,721,051 B2 * | 4/2004 | Menguç et al. | 356/368 |
| 7,142,298 B2 * | 11/2006 | Nuspliger | 356/338 |
| 2001/0014436 A1 * | 8/2001 | Lemelson et al. | 431/12 |

FOREIGN PATENT DOCUMENTS

| | | |
|---|---|---|
| DE | 198 09 789 A1 | 9/1999 |
| WO | 89/00286 A1 | 12/1989 |
| WO | 99/64841 A1 | 12/1999 |

* cited by examiner

*Primary Examiner* — Sang Nguyen
(74) *Attorney, Agent, or Firm* — Ladas & Parry LLP

(57) ABSTRACT

A method for determining size and composition of a particulate matter in a fume flow produced by a combustion process. A polarized laser light beam is projected through the fume flow and the scattered light from the fume flow is gathered in a sideward scattering direction and in at least one forward scattering direction. For each of these scattering directions, the gathered light is separated into two polarized light components on the planes parallel and orthogonal to the scattering direction, the light intensity of each of the polarized light components is measured and a scattered light polarization ratio is calculated as a function of the measured light intensities of the polarized light components. The size of the particulate matter and the unburnt carbon percentage in the particulate matter are determined as a function of the calculated scattered light polarization ratios.

15 Claims, 3 Drawing Sheets

METHOD AND APPARATUS FOR DETERMINING SIZE AND COMPOSITION OF A PARTICULATE MATTER IN A FUME FLOW

The present invention relates to a method and apparatus for determining size and composition of a particulate matter in a fume flow produced by a combustion process.

In particular, the present invention is advantageously, but not exclusively, applied to the analysis of the physical-chemical features of the ash particles in an exhaust fume flow produced by a combustion process in a coal-fed industrial system, to which the following description explicitly refers without therefore loosing in generality.

BACKGROUND OF THE INVENTION

As known, the ash particles produced by a coal-fed combustion process may comprise a percentage of unburnt carbon. A high percentage of unburnt carbon indicates an incomplete combustion. Furthermore, the size of the ash particles provides further information on the combustion process. Thus, knowing the physical-chemical features of the ash particles in the fume flow produced by a combustion process would allow to control the combustion process itself in real time, so as to improve the process efficiency.

Apparatuses for analyzing particulate matter, e.g. ash particles, in the fume flow of a combustion process in real time are known. These apparatuses include projecting a laser light beam through the fume flow, detecting the intensity of the laser light once it has crossed the fume flow, and determining the concentration of particulate matter in the fumes. Unfortunately, these apparatuses do not allow to determine other physical-chemical features, such as the size of the ash particles or the unburnt carbon percentage in the ash particles.

SUMMARY OF THE INVENTION

It is the object of the present invention to provide a method and device for determining size and composition of a particulate matter in a fume flow produced by a combustion process, which is free from the above-described drawbacks while being easy and cost-effective to be implemented.

In accordance with the present invention, a method and device for determining size and composition of a particulate matter in a fume flow produced by a combustion process is provided as defined in the attached claims.

BRIEF DESCRIPTION OF THE DRAWINGS

For a better understanding of the present invention, a preferred embodiment will now be described merely by way of non-limiting example, and with reference to the accompanying drawings, in which.

DETAILED DESCRIPTION OF THE INVENTION

Figure 1:
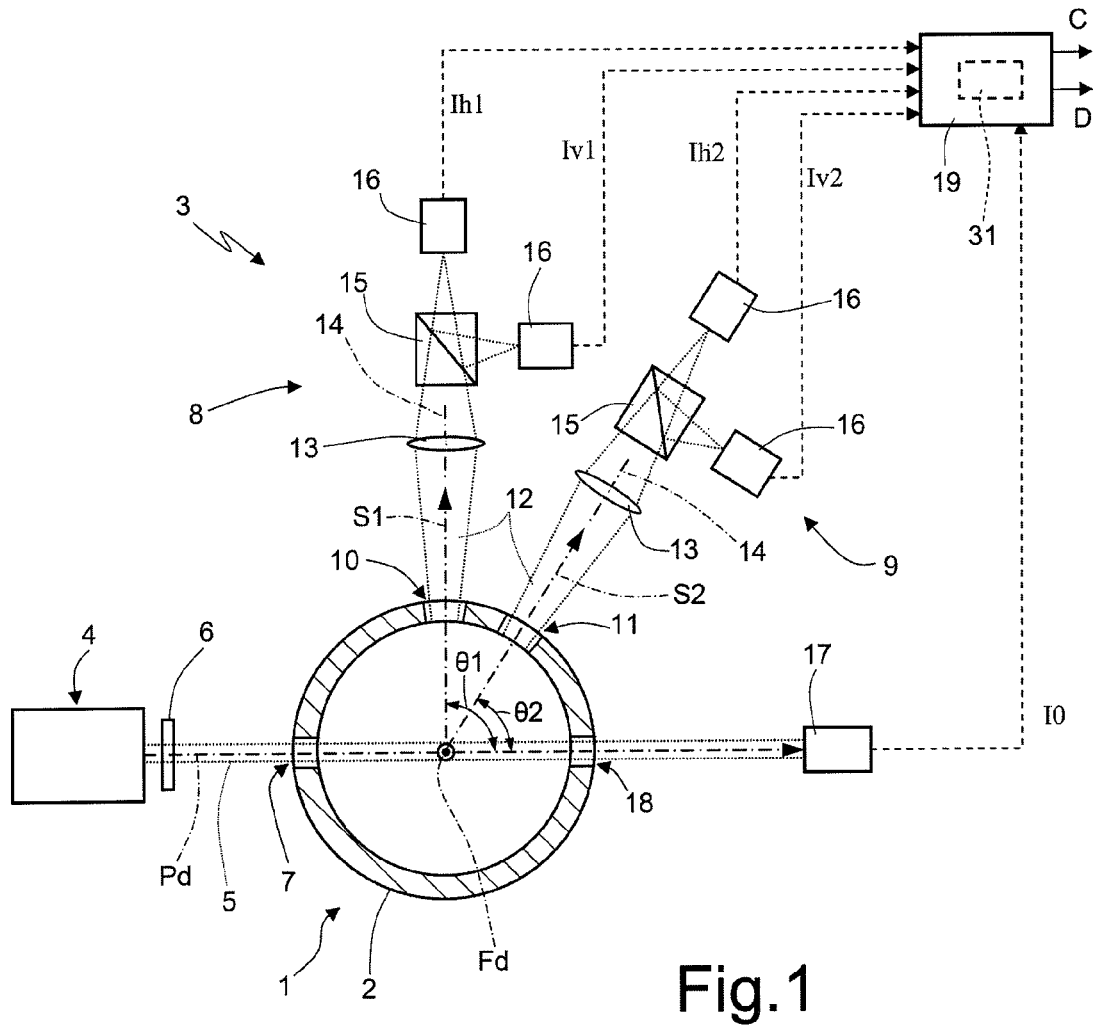
FIG. 1 shows a diagram of the apparatus implementing the method for determining size and composition of a particulate matter in a fume flow in accordance with the invention.

In FIG. 1, reference numeral 1 generally indicates a portion of a chimney for conveying a fume flow produced by a combustion process in a coal-fed industrial system, and in particular a coal-dust-fed system. The chimney portion 1 is shown in cross section. Chimney portion 1 consists of a circular section tube, i.e. the chimney portion has a cylinder-shaped side wall 2. Chimney portion 1 is adapted to convey the fume flow in a fume conveying direction Fd orthogonal to the cross section view in FIG. 1.

The fume flow further comprises, in addition to various gaseous substances, a particulate matter produced by the combustion process. The particulate matter essentially comprises ash particles produced by the combustion process. More specifically, the particulate matter comprises ash particles produced by the combustion of coal dust and unburned particles of the same coal dust. The ash particles have an average distribution size from 10 to 20 $\mu$m and are typically smaller than 100 $\mu$m. The ashes consist of inorganic material and are fairly transparent to visible spectrum radiation, because the imaginary part k of the complex refraction index, which is the specific absorption of the material, is typically in the range from 0.0001 to 0.001. On the contrary, carbon particles are highly absorbent to radiation in the visible spectrum, because the imaginary part k of the complex refraction index is higher, typically in the range from 0.1 to 0.8. It will be assumed that the fume flow and the corresponding particulate matter, which are not shown for simplicity and clarity in FIG. 1, are distributed within the chimney portion 1 in a substantially uniform manner across the whole inner section of the chimney portion 1.

Again in FIG. 1, reference numeral 3 indicates an apparatus 3 for determining size and composition of a particulate matter in a fume flow, which apparatus 3 is provided according to the invention. In particular, apparatus 3 implements the method for determining size and composition of a particulate matter in a fume flow in accordance with the invention, as described below.

Apparatus 3 comprises a laser source 4 adapted to be arranged so as to project a polarized laser light beam 5 through the fume flow in a projection direction Pd transversal to the fume conveying direction Fd. The laser source 4 emits a laser light beam in the visible spectrum. In particular, laser source 4 emits a laser light beam having a wavelength in the range from 600 to 660 nm (red light). Advantageously, laser source 4 is a Neon-Helium (Ne—He) laser source for emitting laser light at a wavelength of 632 nm. Laser source 4 comprises a half-wave plate 6 for polarizing the laser light beam 5 at 45°. Laser source 4 is positioned at an optical inlet 7 obtained in the side wall 2 of chimney portion 1, so that the chimney portion 1 may receive the laser light beam 5 in the projection direction Pd.

Apparatus 3 comprises two optical devices 8 and 9 for detecting the intensity of the scattered light from the fume flow in two different scattering directions forming two respective angles, with the projection direction Pd. The two optical devices 8 and 9 are arranged so as to gather the scattered light from the fume flow in a sideward scattering direction S1 and in a forward scattering direction S2 with respect to the projection direction Pd. Two optical outlets 10 and 11 are obtained in the side wall 2 of the chimney portion 1 for outputting the light scattered in the sideward scattered direction S1 and in the forward scattering direction S2, respectively. The scattered light to be gathered from the optical outlets 9 and 10 is represented by conical light beams indicated by reference numeral 12. Each optical device 8, 9 is adapted to separate the light gathered in the respective scattering direction S1, S2 into two polarized light components on the planes parallel and orthogonal to the scattering direction S1, S2. Finally, each optical device 8, 9 is adapted to measure the light intensity of each of the corresponding polarized light components for the respective scattering direction S1, S2. Due to the average size of the particulate matter to be analyzed (10-20 μm), the light outputted from the optical outlets 10 and 11 is essentially scattered by the particulate matter in the fume flow. Therefore, the detected light intensities essentially depend on the features of the particulate matter.

Again with reference to FIG. 1, each optical device 8, 9 comprises a respective group of lenses, which is indicated by reference numeral 13 and is diagrammatically illustrated as a single lens to gather the scattered light 12 according to a respective optical axis 14. Each optical device 8, 9 further comprises a respective light beam separator 15 of the known type to separate the light gathered in the two polarized light components on the planes parallel and orthogonal to the optical axis 14, and a respective pair of optical detectors 16 for measuring the light intensity of the polarized light components. Each optical detector 16 consists of a photomultiplier. Hereinafter, the measured light intensities of the polarized light components on the planes parallel and perpendicular to the sideward scattering direction S1 are indicated by Ih1 and Iv1, respectively, and the measured light intensities of the polarized light components on the planes parallel and perpendicular to the forward scattering direction S2 are indicated by Ih2 and Iv2, respectively.

The group of lenses 13 of the optical device 8 is adapted to be arranged at the optical outlet 10 with the optical axis 14 overlapping the sideward scattering direction S1 and the group of lenses 13 of the optical device 9 is adapted to be arranged at the optical outlet with the optical axis 14 overlapping the forward scattering direction S2. Each group of lenses 13 is placed at a given distance from the respective optical outlet 10, 11, which distance depends on a focal length of the group of lenses 13 itself. The sideward scattering direction S1 forms a scattering angle θ1 between 80° and 120° with the projection direction Pd. Advantageously, the scattering angle θ1 is 90°. The forward scattering direction S2 forms a scattering angle θ2 between 50° and 70° with the projection direction Pd. Advantageously, the scattering angle θ2 is 60°.

Apparatus 3 comprises a further optical detector 17 for measuring the intensity of the light scattered from the fume flow in a scattering direction coinciding with the projection direction Pd. For this purpose, the optical detector 17 is arranged at a further optical outlet 18 obtained in the side wall 2 of the chimney portion 1 in a position which is diametrically opposite to the optical inlet 7 to output the scattered light in the projection direction Pd. The light intensity measured in such a direction is indicated hereinafter by I0.

Apparatus 3 further comprises a processing unit 19, which is connected to the optical detectors 16 for receiving the measured light intensities Ih1, Iv1, Ih2 and Iv2, and is configured to determine a scattered light polarization ratio PR1 related to the scattering direction S1 as a function of the measured light intensities Ih1 and Iv1, and a scattered light polarization ratio PR2 related to the scattering direction S2 as a function of the measured light intensities Ih2 and Iv2. Furthermore, the processing unit 19 is configured to determine the size of the particulate matter and the unburnt carbon percentage in the particulate matter as a function of the scattered light polarization ratios PR1 and PR2. The processing unit 19 is also configured to determine the concentration of particulate matter in the fume flow as a function of the light intensity 10 measured by the optical detector 17.

Figure 2:
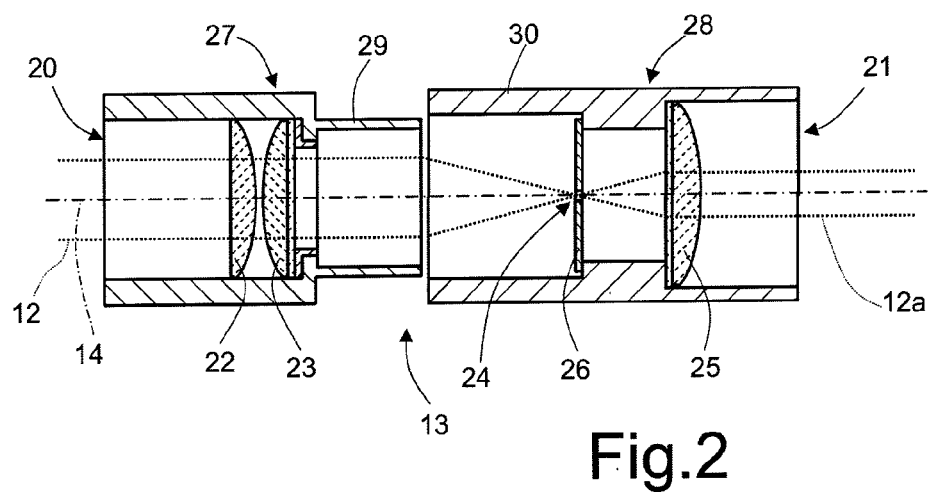
FIG. 2 shows a longitudinal section view of the structure of a group of lenses of the apparatus in FIG. 1.

With reference to FIG. 2, each group of lenses 13 comprises an inlet window 20 for receiving the scattered light 12 to be gathered and an outlet window 21 for outputting the gathered scattered light 12a. Each group of lenses 13 comprises a first piano-convex lens 22, a second piano-convex lens 23, a pin hole 24 and a third plano-convex lens 25 orderly arranged from the inlet window 20 to the outlet window 21 and coaxially with the optical axis 14. Pin-hole 24 is obtained in the middle of a respective disc 26 which is opaque to light and orthogonal to the optical axis 14. Each group of lenses 13 is placed at a given distance from the respective optical outlet 10, 11 of the chimney portion 1 (FIG. 1) equal to the focal length of lens 22.

More in detail, the group of lenses 13 comprises two cylindrical bodies 27 and 28 for accommodating the elements 22-26. The cylindrical body 27 has the inlet window 20 at one end and a first tubular portion 29 at the opposite end. The cylindrical body 28 has a second tubular portion 30 having a diameter larger than the tubular portion 29 at one end, and the outlet window 21 at the opposite end. The tubular portion 29 is slidingly engaged in the tubular portion 30 so as to obtain an optical, structural coupling between the two cylindrical bodies 27 and 28. Cylindrical body 28 accommodates the lenses 22 and 23 and cylindrical body 29 accommodates disc 26 and lens 25. The tubular portions 29 and 30 have a length such as to allow, by sliding within each other along the optical axis 13, to adjust the distance between the pair of lenses 22 and 23 and the pin hole 24.

Lens 22 has the flat side facing the inlet window 20. Lens 23 has the convex side facing the convex side of lens 22. Lens 25 has the convex side facing the outlet window 20. Lens 22 has a focal length in the range from 180 to 220 mm, lens 23 has a focal length in the range from 45 to 55 mm, and lens 25 has a focal length in the range from 13 to 17 mm. Pin hole 24 has a diameter in the range from 500 to 700 μm. Advantageously, lens 22 has a focal length of 200 mm, lens 23 has a focal length of 50 mm, and lens 25 has a focal length of 15 mm. Advantageously, pin hole 24 has a diameter of 600 μm.

The distance between the pin hole 24 and the flat side of lens 23 measured along the optical axis 14 is adjustable by virtue of the above-described coupling in the range from 40 and 80 mm. The distance between the pin hole 24 and the flat side of lens 25 measured along the optical axis 14 is between 10 and 20 mm. Advantageously, pin hole 24 is arranged at a distance of 50 mm from the flat side of lens 23 and at a distance of 15 mm from the flat side of lens 25.

The above-described structure of the group of lenses 13 forms in practice a small telescope capable of gathering the scatted light according to the optical axis 14 while avoiding undesired light beams from being detected by the respective light detector 16.

With regards to the processing operations carried out by the processing unit 19, the polarization ratios PR1 and PR2 are calculated by means of the formulae $$PR1 = (Ih1 - Ihb1)/(Iv1 - Ivb1), \qquad (1)$$

$$PR2 = (Ih2 - Ihb2)/(Iv2 - Ivb2), \qquad (2)$$

where Ihb1 and Ivb1 are background light intensities related to the polarized light components of the scattering direction S1, and Ihb2 and Ivb2 are the background light intensities related to the polarized light components of the scattering direction S2.

The background light intensities Ihb1, Ivb1, Ihb2 and Ivb2 take into account the background scattering due to the air and to the multiple reflections inside the chimney portion 1 in the absence of the fume flow, and are experimentally determined during a step of initial calibration of apparatus 3. In particular, during the step of initial calibration, the laser light beam 5 is projected into the chimney portion 1 through the optical inlet 7 in the absence of the fume flow, the scattered light in the absence of the fume flow is gathered, by means of the optical devices 8 and 9, from the optical outlets 10 and 11, and the light intensities related to the polarized light components produced in the absence of the fume flow in the two scattering directions S1 and S2 are measured. The measured light intensities thus coincide with the background light intensities Ihb1, Ivb1, Ihb2 and Ivb2.

The size of the particulate matter is determined as a function of the scattered light polarization ratio PR1 related to the sideward scattering direction S1. The size of the particulate matter is the diameter D of the particles forming the particulate matter.

In particular, the processing unit 19 stores, in an internal memory 31 thereof, a table which associates the scattered light polarization ratio values with diameter values of the particulate matter particles to be analyzed, e.g. the ash particles produced by a combustion process. The table data may be obtained by means of a relation which binds the scattered light polarization ratio for the sideward scattering direction S1 to the diameter of the particulate matter particles to be analyzed having a given complex refraction index. Such a relation may be determined on the basis of the so-called Mie theory, assuming that the particulate matter is monodisperse, i.e. consisting of particles having the same size. Processing unit 19 thus estimates the diameter of the particulate matter particles by means of the stored table by using the polarization ratio PR1 as an input datum.

Figure 3:
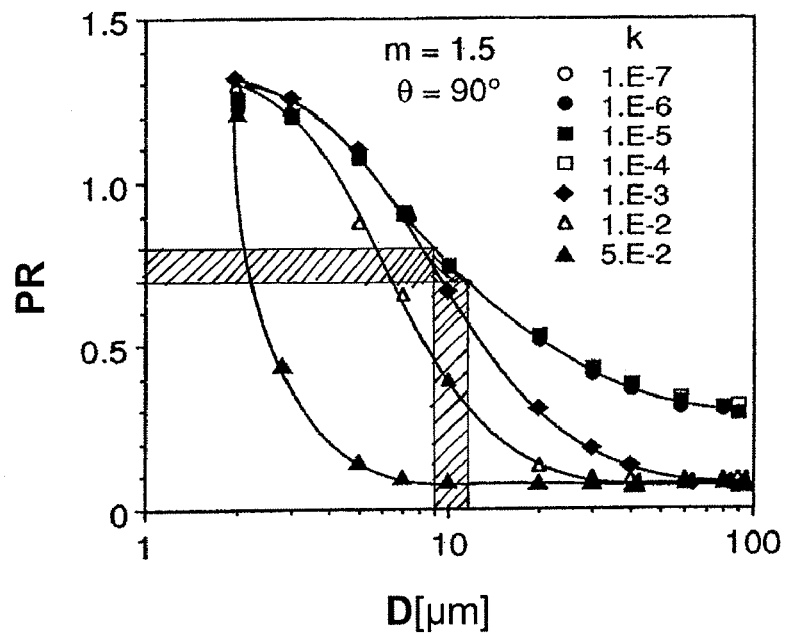
FIG. 3 is a graph showing a scattered light polarization ratio according to the variation of diameter of the particulate matter particles, obtained for a given sideward scattering direction.

FIG. 3 is a graph of the scattered light polarization ratio PR according to the variation of particle diameter D obtained for a scattering angle θ of 90° (sideward scattering). The graph shows a series of curves obtained according to the variation of the complex refraction index of the particulate matter, and in particular of a real index part m equal to 1.5 and for different values of the imaginary part k of the complex refraction index. These curves are obtained by simulation on the basis of a model which assumes particles having different diameters D. The ash particles have an imaginary part k typically smaller than 0.001, while the carbon particles have an imaginary part k between 0.1 and 0.8. Therefore, the carbon particles which are typically larger than 10 μm, are characterized by a very low polarization ratio PR (about 0.1) substantially independent from diameter D, at a scattering angle of 90°. On the other hand, the ash particles which are typically smaller than 10-20 μm, are characterized by a high value of the polarization ratio PR depending on the diameter, at a scattering angle of 90°. Therefore, the polarization ratio PR at the scattering angle of 90° allows to discriminate between carbon and ash particles, and to further determine the diameter D of the ash particles by means of the curves in FIG. 3.

The unburnt carbon percentage in the particulate matter is determined as a function of the scattered light polarization ratio PR2 related to the forward scattering direction S2. In particular, the unburnt carbon percentage in the particular matter, indicated hereinafter by letter C, is determined by means of a linear relation which expresses the scattered light polarization ratio PR as the unburnt carbon percentage varies in the particulate matter, of the type $$PR = A \cdot C + B. \quad (3)$$

Coefficients A and B are determined by means of a linear regression of experimental test results in which the scattered light polarization ratio in the forward scattering direction S2 is determined for various particulate matter samples having different unburnt carbon percentages. Processing unit 19 thus estimates the unburnt carbon percentage C by means of the linear relation (3) using the polarization ratio PR2 as an input datum.

Figure 4:
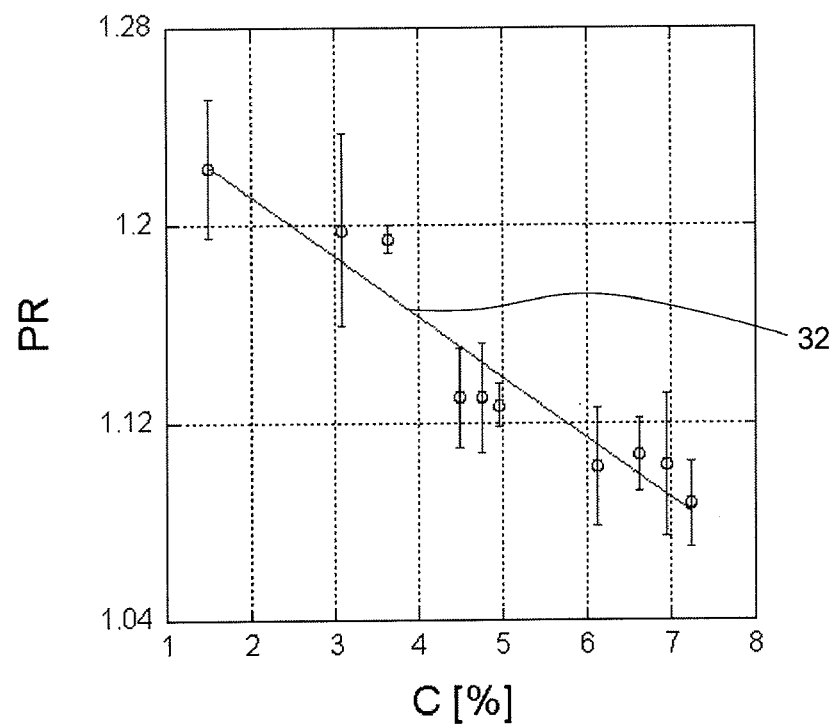
FIG. 4 is a graph showing experimental data related to scattered light polarization ratios for various samples of ash particles obtained for a given forward scattering direction.

FIG. 4 is a graph showing an example of experimental data related to the scattered light polarization ratio PR according to the variation of the unburnt carbon percentage C in the ash particles, which experimental data result from measurements carried out at a scattering angle of 60° for various samples of ash particles. The graph shows a straight line, indicated by reference numeral 32, which is the linear relation (3) obtained by means of the linear regression of the experimental data. According to such an example, coefficient A is −0.024 and coefficient B is 1.26.

Figure 5:
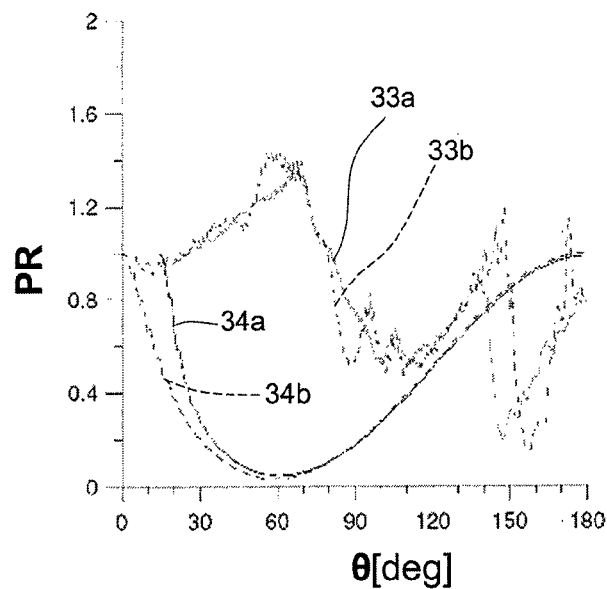
FIG. 5 is a graph showing a scattered light polarization ratio according to the variation of scattering angle in case of ash particles and carbon particles.

FIG. 5 shows curves of the scattered light polarization ratio PR according to the variation of the scattering angle θ in the case of ash particles (which curves are indicated by 33a and 33b) and in the case of carbon particles (which curves are indicated by 34a and 34b). These curves are obtained by simulation on the basis of a model which assumes particles having the same diameter of 20 μm. Two curves are shown for each type of particulate matter (ash or carbon), obtained for two different numerical openings of the groups of lenses 13. Curves 33a and 34a were obtained with a numerical opening of 15°, and curves 33b and 34b are obtained with a numerical opening of 5°. The curves in FIG. 5 show that the carbon particles have a behavior which, from the point of view of the scattered light polarization at scattering angles of about 60°, is complementary to that of the ash particles. Such a complementary behavior confirms the existence of a relation between the scattered light polarization ratio at 60° and the percentage of carbon C in the ash particles.

Figure 6:
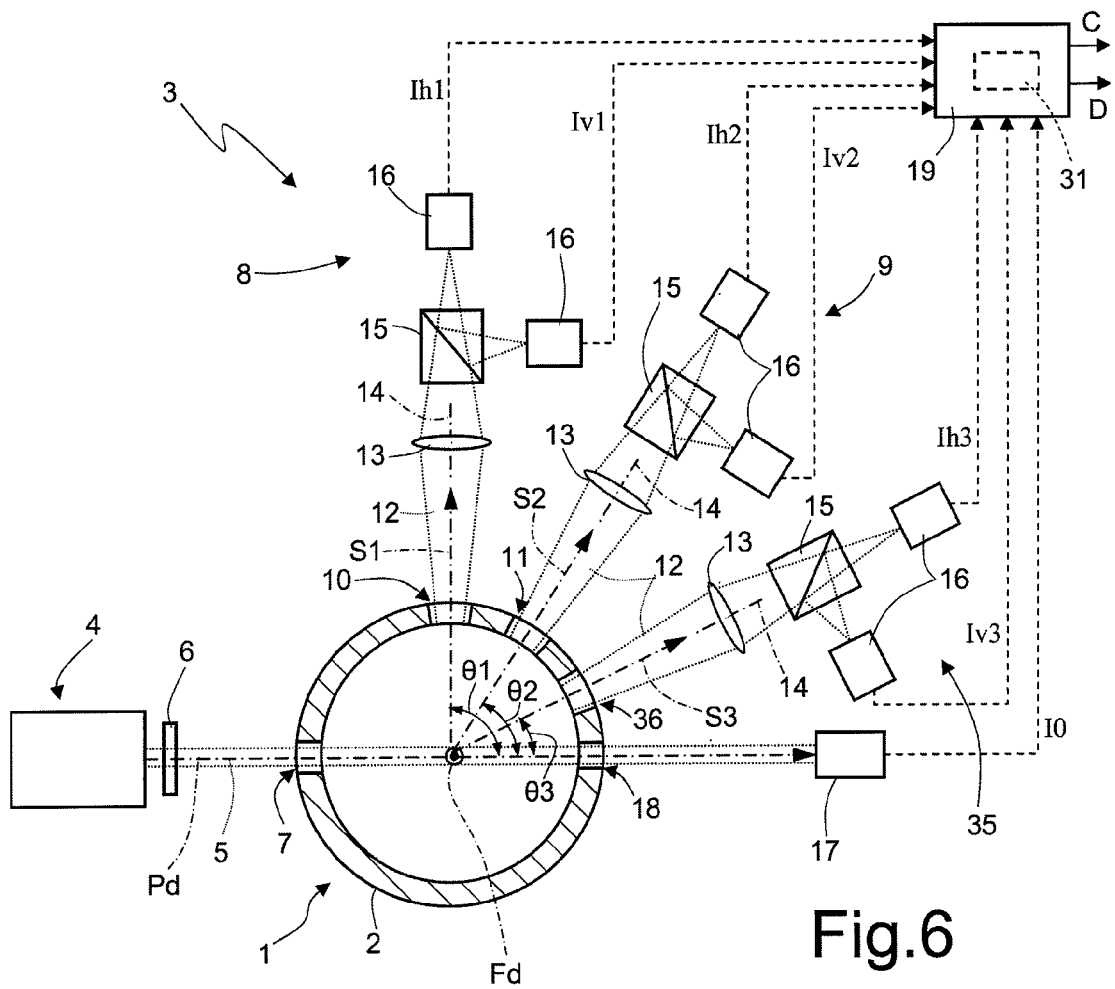
FIG. 6 is a further embodiment of the apparatus in FIG. 1.

According to a further embodiment of the present invention shown in FIG. 6, in which corresponding elements are indicated by the same numbers and codes as FIG. 1, apparatus 3 comprises a third optical device 35 arranged so as to gather the scattered light from the fume flow in a forward scattering direction S3. A further optical outlet 36 is obtained in the side wall 2 of the chimney portion 1 to output the scattered light in the forward scattering direction S3. The group of lenses 13 of the optical device 35 is adapted to be arranged at the optical outlet 36 with the optical axis 14 thereof coinciding with the forward scattering direction S3. The scattering direction S3 forms a scattering angle θ3 between 20° and 40° with the projection direction Pd. Advantageously, the scattering angle θ3 is 30°. Optical detector 16 of the optical device 35 outputs the measured light intensities Ih3 and Iv3 of the polarized light components related to the scattering direction S3. Processing unit 19 substantially performs the same processing operations described above and furthermore is configured to determine a scattered light polarization ratio PR3 as a function of the measured light intensities Ih3 and Iv3 and to determine the unburnt carbon percentage C in the particulate matter as a function of the scattered light polarization ratios PR2 and PR3 determined for the two forward scattering directions S2 and S3. In particular, the unburnt carbon percentage C is estimated by means of the linear relation (3) by using the polarization ratio PR2 as an input datum, and the result is checked by using the polarization ratio PR3.

According to a further embodiment of the present invention based on apparatus 3 in FIG. 6, two values of unburnt carbon percentage C are determined as a function of polarization ratios PR2 and PR3, respectively, and the distribution of the particulate matter is monitored in the fumes inside chimney 1 as a function of these two determined values of unburnt carbon percentage C. This allows to monitor whether the distribution of particulate matter in the fumes is more or less uniform within chimney 1. Indeed, the two optical devices 9 and 35 arranged according to two forward scattering directions S2 and S3 optically target the fume volumes in chimney 1, which are overlapping but not coinciding.

Determining the unburnt carbon percentage C using the two polarization ratios PR2 and PR3 obtained for two respective forward scattering directions S2 and S3 is justified in FIG. 5, which shows that the ash particles and the carbon particles have a complementary behavior also for scattering angles of about 30°.

From the above description, it is apparent that apparatus 3 and, in general, the method implemented by apparatus 3 may also be used to determine the size and composition of particulate matters other than ash, produced by different combustion processes, e.g. fine dust known with the codes PM10, PM5 and PM2.5. To do this, the data table stored in the internal memory 31, which table is used to determine the diameter of the particulate matter particles, is simply replaced with a similar table re-determined on the basis of a different particulate matter, the forward scattering directions S2 and S4 are varied according to the different particulate mater, and the linear relation (3) is re-determined on the basis of the different particulate matter.

The invention claimed is:

1. A method for determining size and composition of a particulate matter in a fume flow produced by a combustion process, the method comprising:
    projecting a polarized laser light beam through the fume flow in a projection direction transversal to a fume conveying direction
    gathering the scattered light from the fume flow in a sideward scattering direction and in at least one forward scattering direction with respect to the projection direction;
    separating, for each of said scattering directions, the gathered light into two polarized light components on the planes parallel and orthogonal to the scattering direction;
    measuring, for each of said scattering directions, the light intensity of each of the corresponding polarized light components;
    calculating, for each of said scattering directions, a respective scattered light polarization ratio as a function of the light intensities of the polarized light components measured for the scattering direction; and
    determining the size of the particulate matter and the unburnt carbon percentage in the particulate matter as a function of the scattered light polarization ratios determined for said scattering directions.

2. The method according to claim 1, wherein determining the size of the particulate matter and the unburnt carbon percentage in the particulate matter comprises:
    determining the size of the particulate matter as a function of the scattered light polarization ratio related to said sideward scattering direction.

3. The method according to claim 1, wherein said particulate comprises ash particles produced by said combustion process; determining the size of the particulate matter and the unburnt carbon percentage in the particulate matter comprises:
    predetermining values of the scattered light polarization ratio related to said sideward scattering direction for corresponding diameter values of ash particle by means of a relation which binds the polarization ratio, the diameter of these particles and the complex reflection index of these particles to one another; and
    estimating the diameter of the ash particles according to predetermined values of the scattered light polarization ratio and of the particle diameter using the scattered light polarization ratio calculated for said sideward scattering direction as an input datum.

4. The method according to claim 1, wherein determining the size of the particulate matter and the unburnt carbon percentage in the particulate matter comprises:
    determining the unburnt carbon percentage in the particulate matter as a function of the scattered light polarization ratio related to said at least one forward scattering direction.

5. The method according to claim 1, wherein determining the size of the particulate matter and the unburnt carbon percentage in the particulate matter comprises:
    determining two coefficients by means of a linear regression of experimental test results wherein the scattered light polarization ratio related to said at least one forward scattering direction is determined for various particulate samples having different unburnt carbon percentages; and
    determining the unburnt carbon percentage as a function of the scattered light polarization ratio calculated for said at least one forward direction of scattering by means of a linear relation of the type $$PR = A \cdot C + B$$

where A and B are said coefficients, C is the unburnt carbon percentage and PR is the polarization ratio.

6. The method according to claim 1, wherein said laser light beam has a wavelength in the range from 600 to 660 nm.

7. The method according to claim 1, wherein said laser light beam is polarized at 45°.

8. The method according to claim 1, wherein said sideward scattering direction forms a first angle in the range from 80° to 120° with said projection direction.

9. The method according to claim 1, wherein said forward scattering direction forms a second angle in the range from 50° to 70° with said projection direction.

10. The method according to claim 1, wherein said fume flow is conveyed by a chimney along said fume conveying direction; said chimney comprising a side wall, in which an optical inlet for receiving the laser light beam in said projection direction, a first optical outlet for outputting the scattered light in said sideward scattering direction, and at least one second optical outlet for outputting the scattered light in said at least one forward scattering direction are obtained; the method further comprising:
    projecting said polarized laser light beam in the chimney through the optical inlet in the absence of the fume flow;
    gathering the scattered light in the absence of the fume flow from the optical outlets; and
    measuring, for each of said scattering directions, the background light intensity of each of the corresponding polarized light components produced in the absence of the fume flow;

each said scattered light polarization ratio being also determined as a function of the background light intensities of the polarized light components.

11. The method according to claim 1, wherein said scattered light from the fume flow is gathered in at least two forward scattering directions; determining the size of the particulate matter and the unburnt carbon percentage in the particulate matter comprising:
   determining the unburnt carbon percentage in the particulate matter as a function of the scattered light polarization ratios determined for the two forward scattering directions.

12. The method according to claim 11, wherein said two forward scattering directions form a second angle in the range from 50° to 70° and a third angle in the range from 20° to 40°, respectively, with said projection direction.

13. An apparatus for determining size and composition of a particulate matter in a fume flow produced by a combustion process and conveyed by means of a chimney; the apparatus comprising a laser source for projecting a polarized laser light beam through the fume flow in a projection direction transversal to a fume conveying direction, and at least two optical devices for detecting the intensity of the scattered light from the fume flow in a sideward scattering direction and in at least one forward scattering direction; each optical device comprising a respective group of lenses for gathering light according to a respective optical axis, a respective light beam separator for separating the gathered light into polarized light components on the planes parallel and orthogonal to the optical axis, and a respective pair of optical detectors for measuring the light intensity of the polarized light components; the group of lenses of a first optical device being arranged with the optical axis overlapping the sideward scattering direction, and the group of lenses of the second optical device being arranged with the optical axis overlapping the forward scattering direction; the apparatus further comprising a processing unit, which is connected to the optical detectors for receiving the measured light intensities and is configured to determine, for each of said scattering directions, a respective scattered light polarization ratio as a function of the light intensities of the polarized light components measured for the scattering direction, and to determine the size of the particulate matter and the unburnt carbon percentage in the particulate matter as a function of the scattered light polarization ratios determined for said scattering directions.

14. The apparatus according to claim 13, and comprising at least three optical devices for detecting the intensity of the scattered light from the fume flow in a sideward scattering direction and in at least two forward scattering directions; the group of lenses of the second and third optical devices being arranged with the respective optical axis overlapping a respective forward scattering direction.

15. An apparatus according to claim 13, wherein each said group of lenses comprises an inlet window for receiving the scattered light to be gathered and an outlet window for outputting the gathered scattered light; each group of lenses comprising a first plano-convex lens, a second plano-convex lens, a pinhole and a third plano-convex lens orderly arranged from the inlet window to the outlet window and coaxially to said optical axis.

* * * * *